United States Patent [19]

Fettel

[11] 4,057,857
[45] Nov. 15, 1977

[54] HEART VALVE WITH ARCUATE OCCLUDER

[75] Inventor: Bruce E. Fettel, Diamond Bar, Calif.

[73] Assignee: Shiley Laboratories, Inc., Irvine, Calif.

[21] Appl. No.: 611,273

[22] Filed: Sept. 8, 1975

[51] Int. Cl.² .............................................. A61F 1/22
[52] U.S. Cl. ...................................... 3/1.5; 137/527.8
[58] Field of Search .............. 3/1.5, 1; 137/527, 527.8

[56] References Cited

U.S. PATENT DOCUMENTS

| 3,824,629 | 7/1974 | Shiley | 3/1.5 |
| 3,926,215 | 12/1975 | Macleod | 3/1.5 X |

FOREIGN PATENT DOCUMENTS 1,327,371  8/1973  United Kingdom ................ 137/527

*Primary Examiner*—Ronald L. Frinks
*Attorney, Agent, or Firm*—Knobbe, Martens, Olson, Hubbard & Bear

[57] ABSTRACT

A convexo-concave, saucer-like heart valve vane is floatingly supported in a valve ring between a vane closing support rod, which engages the edge of a concentric recess on the arcuate convex side of the vane, and a vane closing support rod which engages the arcuate concave side of the vane. In its open position, the limiting portion of the convex distal surface of the vane is nearly aligned with the blood stream to maximize the blood flow through the portion of the valve defined by said portion and the adjacent portion of the ring.

12 Claims, 7 Drawing Figures

HEART VALVE WITH ARCUATE OCCLUDER

Beginning in about 1960, the use of heart valve prosthesis emerged from a period of experimentation into a period of practical, surgical application. The medical literature in the field of cardiovascular surgery includes numerous surgical procedures and techniques for implanting heart valve prostheses and many heart valve prostheses are described. Reference is made to this body of literature respecting the medical aspects of heart valve prosthesis implantation and usage, specific reference being made to the publication of Professor Viking O. Bjork, in the Scandinavian Journal of Thoracic and Cardiovascular Surgery.

In U.S. Pat. No. 3,824,629-Shiley there is disclosed a heart valve prosthesis having a vane which is eccentrically supported by structure extending inwardly from the surrounding valve ring so as to floatingly contain the vane during opening and closing movement in response to the pumping action of the heart. This application relates to an improvement in such a valve.

The earlier Shiley valve has been highly successful, providing excellent results and becoming well accepted in the medical profession. Such valves have had very little thrombus formation which has been a problem with many of the prior art valves. Nevertheless, there exists the potential in isolated cases for some thrombus formation even with the valve of the above patent. In such isolated cases, thrombus is most likely to occur in areas of the valve which are washed less thoroughly by the blood than the other areas. It is, of course, desirable, if possible, to further reduce the potential for thrombus formation. In the heart valve disclosed in the above mentioned Shiley patent, the vane divides the orifice through the valve ring into two flow areas of unequal size because of the eccentric mounting of the vane. The vane tilts in the range of 50° to 80° from a closed position parallel to the plane of the valve ring into the fully open position. When in this open position, on the proximal side of the valve the leading edge of the vane is oriented at approximately this same opening angle since the vane has a relatively thin cross-section, which tapers towards the edge uniformly on both sides. Consequently, the leading edge of the vane tends to direct a larger proportion of the blood towards the larger area through the orifice than the ratio between the large and small areas of the orifice would indicate. That is, if the smaller area through the valve orifice constitutes 25% of the total area, the smaller area does not necessarily receive 25% of the blood flow. Blood flow through the valve could be increased by opening the vane more fully; however, this may not be advantageous because of the additional travel time required for the vane to open and close.

In accordance with the present invention, the percentage of blood flow through the smaller area of the orifice at a given flow rate through the valve has been increased by changing the configuration of the vane without increasing the pressure gradient across the valve. In particular, the vane is formed with a saucer-like configuration having an arcuate convex surface on one side and an arcuate concave surface on the other, maintaining a very thin profile to obtain rapid valve operation and providing smoothly curved surfaces and lower pressure gradient across the valve. As in the earlier Shiley patent mentioned above, the vane is eccentrically mounted so that the vane in open position creates flow areas through the valve of unequal size. However, the percentage of flow through the smaller orifice area has been increased by arranging the vane so that entrance to the smaller orifice area is increased. The vane is oriented so that the convex surface defines the smaller orifice area in cooperation with the adjacent portion of the valve ring. The tangent to the arcuate convex surface on the leading edge of the vane is substantially aligned with the blood flow when the vane is in its fully open position, with the result that smaller orifice area is fully open to fluid flow and the vane divides the flow with a minimum of turbulence. As mentioned, the pressure gradient across the valve remains at a low level.

In the preferred arrangement, the vane is supported by a pair of support rods extending inwardly from the surrounding valve ring. A vane opening support rod provides a surface engaging a shallow central recess in the convex side of the vane forming an asymmetric knuckle-like joint to enable the vane to tilt around this knuckle during its opening operation. A vane closing support rod is located on the concave side of the vane to form a changing rocker-like contact line for the vane during its closing operation. Because of the convexo-concave configuration of the vane, it is free to move slightly away from the vane orifice in the open position which further minimizes the likelihood of thrombus formation between the vane and the orifice. The central circular recess in the convex side of the vane enables the vane to rotate about a central axis of the vane in its loosely captive arrangement between the two support rods. This provides improved washing of the vane and evenness of wear. The combined arcuate proximal and distal surface arrangement maximizes fluid flow through the smaller area of the valve while maintaining a low pressure drop across the valve.

The arrangement described wherein the upper and lower surfaces of the valve occluder are arcuately configured provides a particularly low pressure gradient across the valve as compared, for example, with a valve in which the distal surface is in the configuration of a right frustocone, having a depression in the top center of the frustum (or the equivalent, a circular depression adjacent the top of the conical surface) and the proximal side of the occluder is configured as the inside of a right frustocone; i.e., having an inwardly slanting circular sidewall and a flat top, as described in the application of Donald P. Shiley, filed concurrently herewith, Ser. No. 611,594, now abandoned. The present invention constitutes a significant improvement over the aforementioned valve having frustoconical distal and proximal surface configurations by substantially improved flow pattern and decreased pressure gradient, thus making the present invention suitable for use in patients whose cardiac pumping capacity has been impaired by disease, damage or otherwise in which considerable additional risk would be inherent in the use of the frustoconically configured valve occluder.

For a more thorough understanding of the heart valve prosthesis of this invention reference may be had to the following detailed description and drawings wherein.

Figure 1:
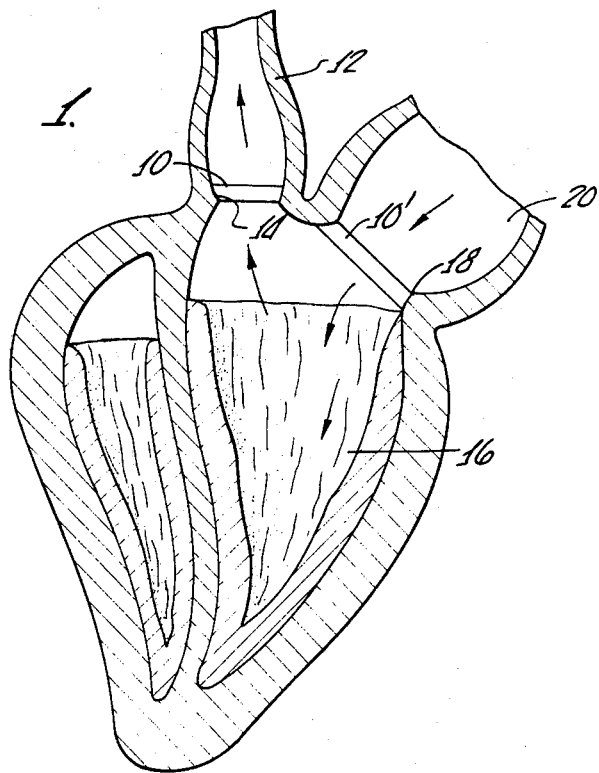
FIG. 1 is a diagrammatic sectional view of a heart with the prostheses of this invention inserted in place of the natural mitral and aortic heart valves.

Although the heart valve prosthesis of this invention is particularly adapted for use as an aortic or mitral valve, as shown diagrammatically in FIG. 1, the prostheses 10 and 10' may be made in various sizes for use either as an aortic, mitral or tricuspid valve replacement. The aortic valve prosthesis 10 is mounted in the aortic artery 12 at the natural valve ring 14 intermediate the aorta 12 and the left ventricle 16. The mitral valve prosthesis 10' is mounted in the left ventrical 16 on the muscle tissue 18 of the natural valve ring intermediate the left ventricle and the left atrium 20. For purpose of illustrating the prosthesis, it will be discussed primarily as an aortic valve replacement.

Figure 2:
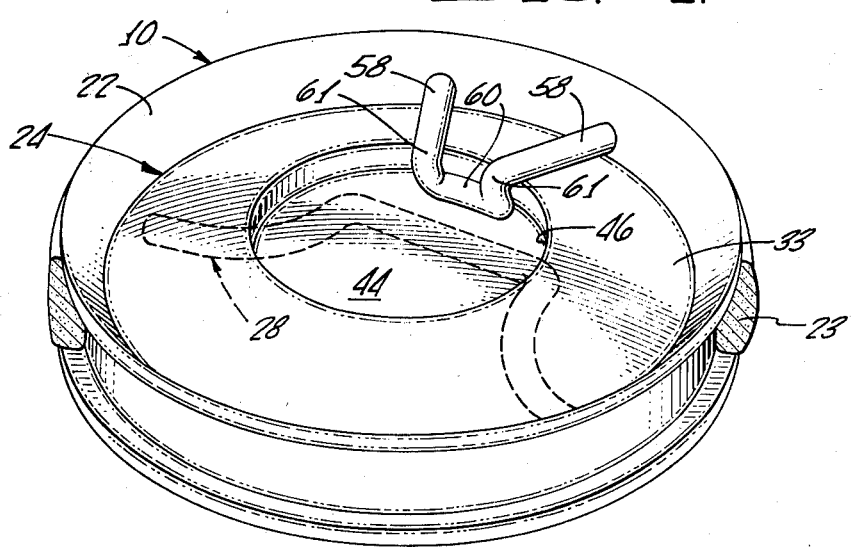
FIG. 2 is a top perspective view of the heart valve prosthesis constructed in accordance with this invention.
Figure 3:
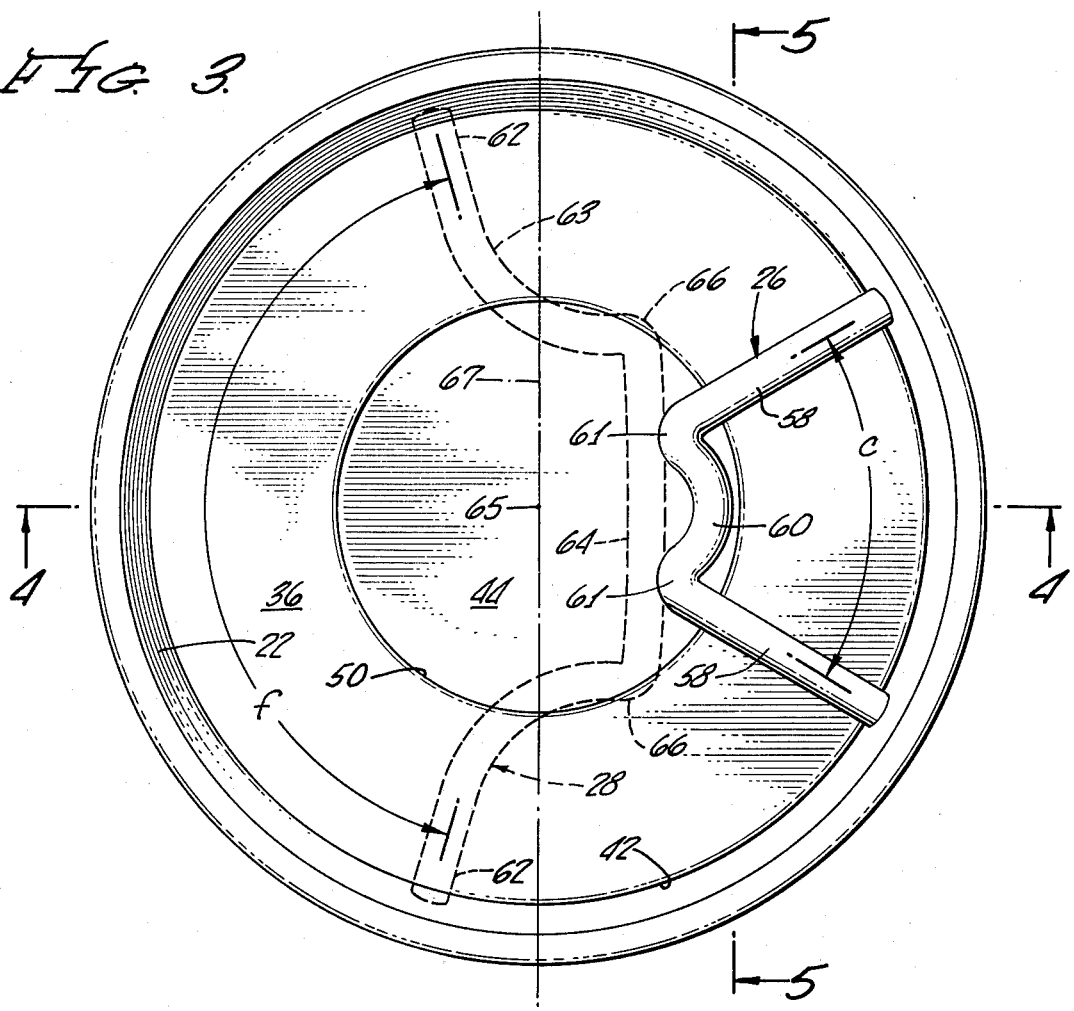
FIG. 3 is a top plan view of the prosthesis of FIG. 2, with the suture ring omitted.
Figure 4:
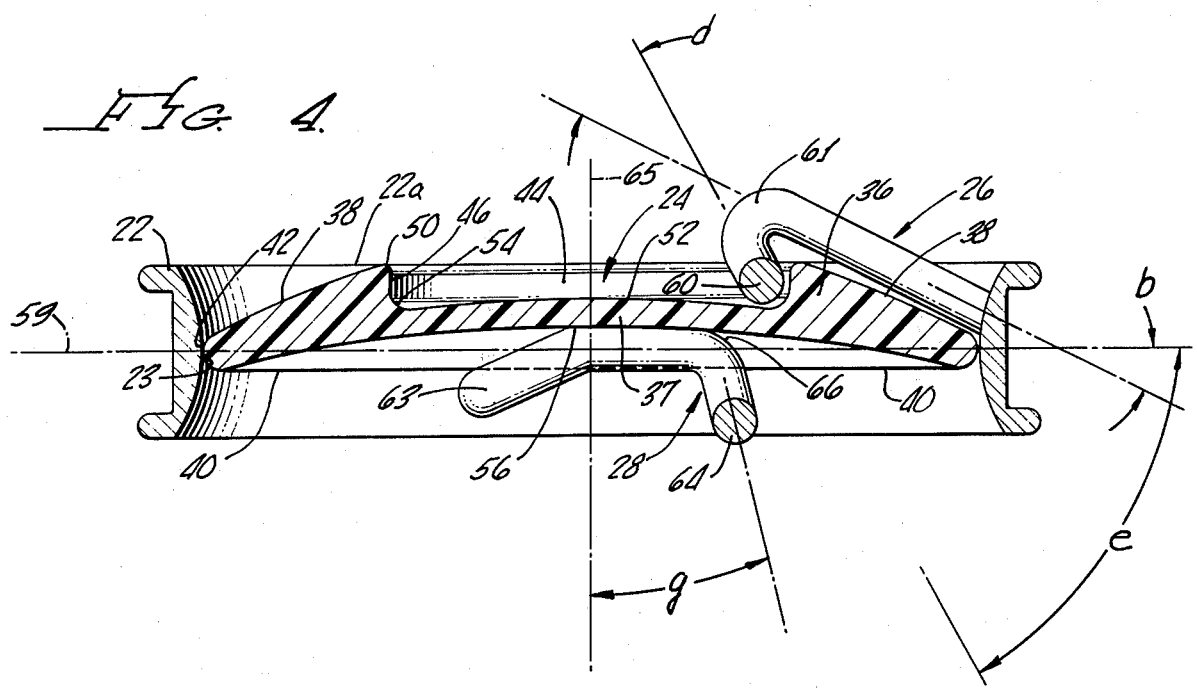
FIG. 4 is a sectional view through the prosthesis of FIG. 3 on lines 4—4.

As shown in FIGS. 2, 3 and 4, the structure of the prosthesis 10 includes a metallic valve ring 22 having an inner wall which defines a valve orifice through which the blood flows as controlled by a movable valve occluder in the form of a discoid vane 24. (The vane is not truly a disc, although that term is loosely applied to the vane, and the term "discoid" is not used in any technical sense but is selected merely to suggest a body which is round, has an overall thickness less than the diameter and has a complex configuration which is not easily described except by function and on a portion by portion basis. Any body which is so configured as to function in the manner described hereinafter may be regarded as discoid.) A vane opening support rod 26 and a vane closing support rod 28 have their ends attached to the valve ring 22 by welding or other suitable means to support the vane for movement within the valve ring 22. Suitable means, such as suture ring 23, is secured about the valve ring for connecting the valve to the heart or aortic tissue. One such arrangement is described in the above mentioned Shiley patent.

From FIG. 4, it may be seen that the valve vane 24 has a convexo-concave, saucer-like configuration, having radial symmetry about a center axis perpendicular to the general plane of the vane, with the convex surface 38 having a concentric recess 44 which creates an annular vane portion 36 and a thinner central portion 37. The distal surface 38 of the vane 24 has a convex curvature formed on a radius of curvature which in a preferred form of the invention is about equal to the diameter of the vane 24. The proximal surface 40 of the vane has a concave curvature about a radius of curvature of which in a preferred form of the invention is generally in the range of two or three times the radius of curvature of the distal convex surface 38.

The peripheral edge 42 of the vane 24 is rounded to lie, in the closed position, adjacent to and, in the preferred form, spaced slightly from the inner surface 23 of the valve ring 22 which forms the orifice through which the blood flows. In a preferred form of the invention, the thickness of the edge 42 where the edge curvature starts is greater than the thickness of the vane central portion 37. This indicates the light weight, low profile of the vane. The ring 22 has the shape of a toroidal section with the inner surface being smoothly rounded to minimize fluid friction losses. The vane is just slightly smaller in diameter than the orifice 23 so that when it is in its closed position, as shown in FIG. 4, it is supported by the rods 26 and 28, and allows a washing backflow through the space thus formed.

The central circular depression or recess 44 in the convex surface 38 is peripherally defined by an annular vertical sidewall 46. The sidewall 46 is connected to the convex surface 38 in a smooth curved shoulder 50 and to the lower wall 52 of the recess 44 by a juncture 54 having a relatively large radius of curvature. The thicker annular portion 36 of the vane is connected to the thinner central portion 37 by the wall 46 intermediate the curved shoulder 50 and the juncture 54.

The vane opening support rod 26 includes diverging portions 58 and a circumferentially curved hook or knuckle portion 60 joined by shoulders 61. The rod portions 58 are secured to the ring 22 on the distal side of the plane 59 through the orifice 23, which plane may also be referred to as the general plane of the ring 22 since both the ring and the orifice are perpendicular to an axial line 65 through the center of the orifice and the ring. The rod portions extend inwardly and distally with the portions 58 forming an angle b of a little under 30° with the plane 59 of the valve. Note that the portions 58 extend distally beyond the edge of the ring 22. The shoulders 61 curve back proximally toward the plane 59, thus forming a smooth curve intermediate the rod portion 58 and the knuckle portion 60. In the preferred embodiment, the rod portions 58 diverge outwardly toward the ring at an angle c of about 60° as shown in FIG. 3. The knuckle portion 60 forms an angle d of a little over 30° with respect to portions 58 and angle of about a 60° angle e with respect to the plane 59. The vane opening rod 26 has a diameter sufficiently large so that its outer surface approximately corresponds to the radius of curvature of the juncture 54. The radius of curvature of the knuckle portion 60 is slightly less than the curvature of the sidewall 46 of the recess 44 which forms the other portion of the asymmetric knuckle as shown in FIG. 3. The knuckle portion 60 is positioned at the edge of the recess 44 and extends into the recess to define a contact surface which supports the vane during opening. As noted from FIG. 4 with the vane 24 in its closed position, its periphery 42 is approximately in the plane of the orifice 23. Because of the vane convex configuration, the vane opening support rod portions 58 extend distally from the edge 22a of the low profile ring 22 and the knuckle 60 of the rod 26 extends into the recess 44 approximately in the plane of the edge of the valve ring 22.

Figure 5:
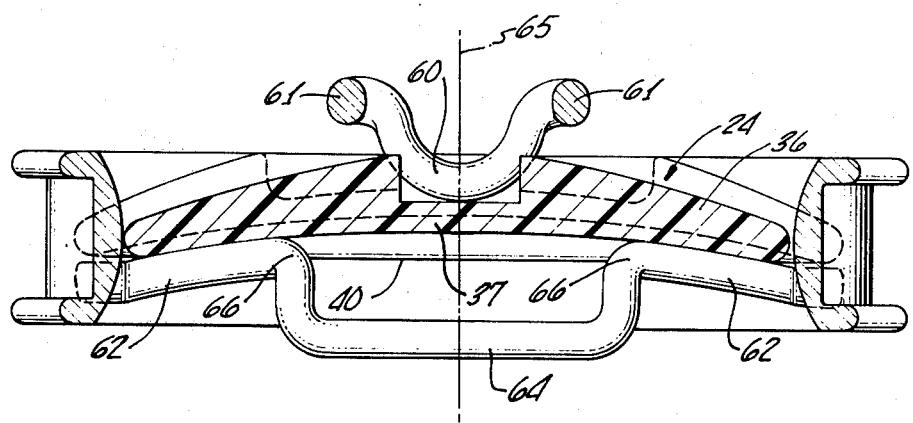
FIG. 5 is a sectional view of the prosthesis of FIG. 3 on lines 5—5.

The vane closing support rod 28 as shown in FIGS. 3, 4 and 5, is a symmetrical, complexly shaped member including essentially straight end portions 62 which are welded or otherwise connected to the ring 22 slightly proximal of the orifice plane 59, which is below the orifice plane in FIGS. 4 and 5, in position to support the vane in its closed position. The straight rod portions 62 extend inwardly from the ring and if continued would pass through the axial center line 65 shown in FIGS. 3 and 4. The angle f formed by the extensions of the end portions 62 as shown in FIG. 2 is about 150° in the preferred embodiment. However, instead of extending straight, the end portions 62 blend into portions 63 which curve. As seen from FIG. 3, the end portions 62 are both shown on one side of a diameter line 67 in the orifice plane 59 with the end portions 62 being equally spaced from the line 67. The portions 63 curve on a rather sharp circular arc inwardly and across the diameter line 67 such that if continued, they would once more intersect the valve ring 22. The curved portions 63 pass through an arc of slightly less than 90° and then connect to a curved central portion 64 by means of smooth curved shoulders 66. As seen from FIG. 4, the curved portions 63 also slope toward and across the orifice plane 59 on a large radius of curvature to conform to the concave surface of the vane 24. The shoulders 66 curve back toward and across the orifice plane at an angle away from the plane or away from the vane 24 when shown in its closed position in FIG. 4. The shoulders 66 angle radially outwardly preferably at an angle $g$ of about 20° with respect to the axial center line 65 of the valve as may be seen in FIG. 4. The central portion 64 connects the shoulders 66 and curves slightly radially outwardly from the axial center line 65 of the valve on a very large radius of curvature in a plane approximately parallel to the orifice plane 59. The various portions of the vane opening rod 28 facing the vane form a continuous smooth, curved, camming surface over which the concave surface 40 of the vane can ride when the vane is being closed. As may be seen from FIG. 4, the camming surfaces on the shoulders 66 are substantially subjacent the opening rod knuckle portion 60 for defining a loose, overcenter rocker support for the vane during closure.

The spacing between the upper shoulders 66 and the knuckle 60 on the vane opening support rod 26 is smaller than the thickness of the thickest part of the annular portion 36 of the vane 24 between the concave-convex vane surfaces so that the vane cannot slip out of the valve assembly. That is, the vane is supported and confined by the rods 26 and 28 in cooperation with the valve ring 22.

Figure 6:
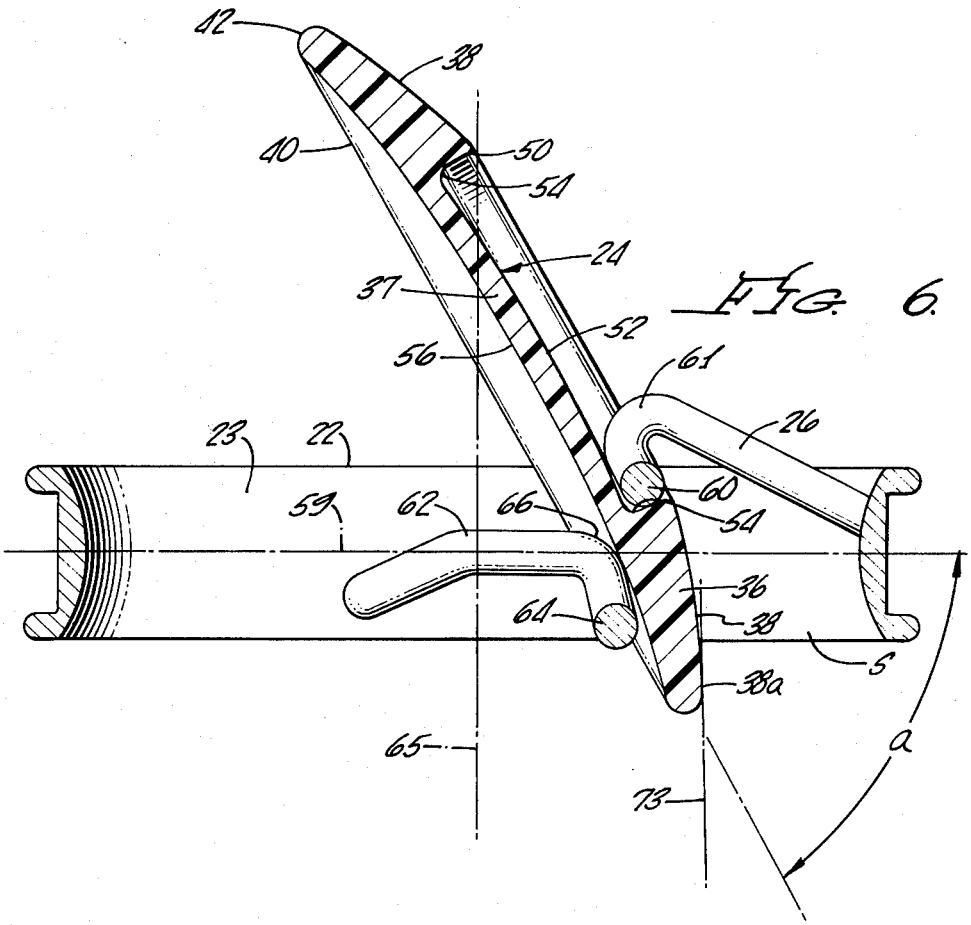
FIG. 6 is a sectional view of the prosthesis similar to FIG. 4 but showing the valve vane in an open position.

During operation of the aortic heart valve prosthesis of this invention, the valve means 24 responds to blood pressure pulses created by the heart. The vane is hemodynamically opened by systolic contraction of the left ventricle which forces blood against the concave proximal surface 40 of the vane. The vane immediately moves away from the lower vane closing support rod 28 and into engagement with the knuckle 60 of the opening support rod 26 in the edge of the central recess 44. The contacting surface is a short circular line contact, an asymmetrical knuckle contact. Since the contact between the vane and the rod is eccentric with respect to the center of the vane or the axial center line 65, the forces acting against the vane tilt the vane open around the knuckle. The opening movement is loosely controlled by the combined action of the knuckle 60 of the opening support rod 26 and the center portion 64 of the closing support rod 28 and the ring 22. The movement during opening is a wobbly tilting action because of the loose fit. This is advantageous because the vane can react to variations in the fluid flow through the valve. As seen in FIG. 6, the center portion 64 of the support rod limits the opening of the vane. Essentially a line contact is formed between the center portion 64 of the proximal support rod and the concave surface of the vane. The vane periphery 42 may also lightly touch a portion of the ring 22 if the vane is off center with respect to the support base 24.

In a preferred embodiment, the spacing between the upper support rod knuckle 60 and the center portion 64 of the proximal support rod is sufficient to enable the valve vane to open to an angle $a$, shown in FIG. 6, of about 60° from the orifice plane. It has been found that the pressure gradient as a function of opening angle is such that satisfactory operation is obtained even if the vane is limited to an opening angle of 50°. An opening angle $a$ in the range from 50° to 80° is quite satisfactory from that standpoint. At values higher than 80°, the pressure gradient is not reduced by an appreciable amount while the response time is increased due to the longer distance the vane must travel.

The fitting of the central curved section of the proximal support rod into the juncture 54 of the recess 44 on the vane enhances the opening motion so that relatively little pressure is required to open the valve. The light weight of the vane and the eccentric mounting of the central portion 60 is such that initial opening gradients are on the order of 2 to 5 millimeters of mercury.

It should be noted that in the valve open position of FIG. 6, the proximal edge of the vane, which is the leading or upstream edge, presents very little blocking or occluding surface to the blood stream. A line 73 which is tangent to the concave vane surface 38 at the point 38a where the concave surface blends into the curvature of the peripheral edge 42 of the vane is approximately parallel to the center line 65 of the valve, which is the predominate direction of blood flow. In practice the tangent 73 may vary a few degrees, e.g., up to 5° to 8° in either direction, from being parallel to the blood stream or the center line 65. As a result, the area $s$ of the opening between the edge of the vane 24 on the proximal side of the valve, as shown in FIG. 6, and the adjacent side of the ring 22 to which the vane opening rod 26 is attached, is considerably increased from the area of the analogous opening in prior valves shown in the above mentioned Shiley patent. In other words, the percentage of blood flow in this smaller orifice area $s$ is defined by the convex surface of the vane and the adjacent ring portion with respect to the total flow through the valve has increased significantly, as much as 50% over the percentage of blood flow through the analogous area in the prior Shiley valve which had vanes with flat or straight sloping sides. The main advantage of this arrangement is that the increased blood flow in this area reduces the chance of thrombus because of the additional washing in that area without increase in the pressure gradient across the valve.

Another advantage of the convexo-concave vane is that the vane extends a considerable distance distally of the valve ring when the vane is in the open position of FIG. 6 because the knuckle 60 of the vane opening support rod 26 is spaced considerably distal of the orifice plane because the shape of the vane positions the vane juncture 54 in the recess 44 at this location. The entire vane 24 is thus positioned downstream further in the valve ring 22 in the vane open position. The importance of this is that the portions of the edge 42 of the vane closest to the valve ring 22 are normally spaced further from the ring than in the prior art valve. Consequently, blood can flow between the edges of the vane and the valve ring thus reducing resistance to flow and, more importantly, further minimizing the likelihood of thrombus formations at those two points. While one portion of the vane edge may touch one portion of the valve ring 22 in the open position, the vane can wobble and move slightly from side to side during repeated opening and closing cycles with the results that increased blood washing is attained between the edges of the vane and the ring 22.

At the onset of diastole, the pressure in the left ventrical drops to zero and the pressure of the blood in the aorta acts in the reverse direction on the vane, causing vane to slip toward the proximal side of the valve out of contact with the distally located opening support rod 26 and to begin to rock close on the camming surface of the proximally located closing support rod. The edge 42 of the vane contacts the ring at two points thus limiting the lateral slip of the vane. Initial contact of the concave surface of the vane 24 and the vane closing support rod 28 is highly eccentric and the initial closing pressure is distributed over a large portion of the vane above the orifice or ring plane 59. As the vane closes, however, the distance between the contact area of the support rod with the surface of the vane and the diameter line 67 of FIG. 3 decreases as the vane engages the shoulder 66, the curved portion 63 and the end portion 62. Immediately prior to closing, the line of contact is at about the diameter line of the vane so that the vane closing forces which act on one half of the convex surface of the vane to close it are obtained by similar forces which act on the other half of the convex surface of the vane and tend to open it. This condition is attributable to the migrating line of contact which moves along the camming surfaces of the vane closing rod 28 as the vane closes in a rocking motion, much as the contact point of the rockers of a rocking chair moves to and fro as the chair is rocked. The closing acceleration of the vane is thus reduced significantly by this migration of the line of contact. The vane opening rod 26 limits the movement of the vane beyond the closed position.

As the vane opens and closes, it momentarily wobbles and floats between the support rods and rotates in the plane of the vane thereby evenly distributing the forces on the vane and reducing problems of thrombosis and protein buildup that is more likely to occur with a fixed hinge vane. That is, with such rotation, the contact between the vane and the support rods 26 and 28 does not always occur at the same point so that all surfaces of the vane continue to be washed thoroughly. This also has the important advantage that wear is evenly distributed on the vane with the result that the projected life of the vane is enhanced.

Table I shows the preferred dimensions, radii, etc., for standard valve sizes and is included as an aid to understanding the invention and for completeness of disclosure with the understanding that these values are exemplary, subject to great variation, and nonlimiting as to the scope of the invention. The values listed are in millimeters and are rounded off to the number of significant figures shown.

TABLE 1

| Valve Size (1) | Vane Dia. (2) | Prox Radius (3) | Distal Radius (4) | Well Dia. (5) | Well Depth (6) | Edge Radius (7) | Webb Thickness (8) |
|---|---|---|---|---|---|---|---|
| 21 | 15.9 | 15.5 | 48.3 | 8.2 | 1.04 | .43 | .76 |
| 23 | 17.7 | 17.3 | 53.5 | 8.9 | 1.07 | .43 | .76 |
| 25 | 19.9 | 19.5 | 47.8 | 10.2 | 1.17 | .43 | .76 |
| 27 | 22.0 | 21.5 | 45.0 | 11.2 | 1.17 | .43 | .76 |
| 29 | 24.0 | 23.6 | 45.0 | 12.1 | 1.17 | .43 | .76 |

(1) Tissue annulus diameter.
(2) Diameter of the Discoid vane.
(3) Radius of curvature of the proximal surface.
(4) Radius of curvature of the distal surface.
(5) Diameter of the central depression or well.
(6) Depth of the central depression or well.
(7) Raidus of curvature of the peripheral edge of the vane.
(8) Thickness of the vane measured from the bottom of the central depression or well to the proximal surface.

Figure 7:
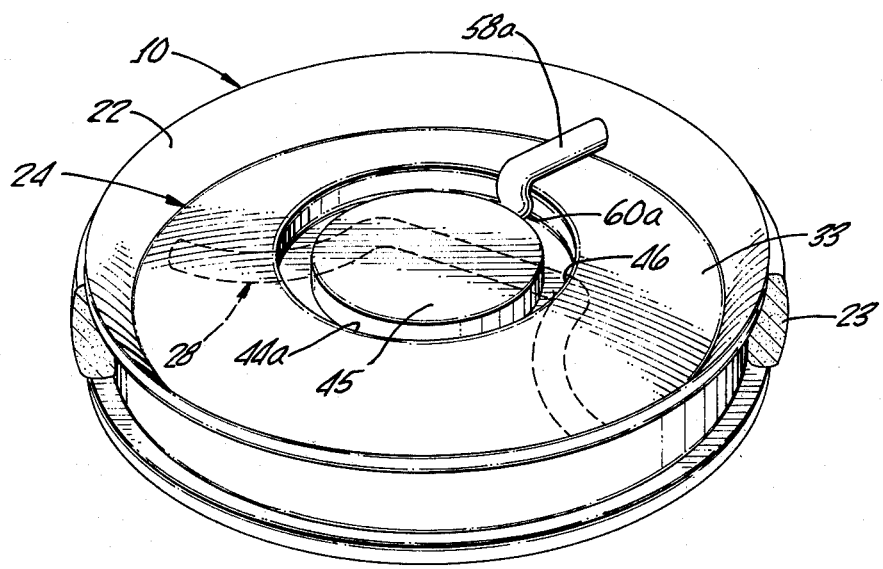
FIG. 7 is a top perspective view of an alternative construction.

The present invention contemplates any number of variations and alternatives to the exemplary structures depicted and described. One illustrative alternative is depicted in FIG. 7 in which the same numerals are used for the structures and features previously described. The exemplary embodiment of FIG. 7 differs from the preferred embodiment previously described in that the strut element 58a replaces the closing rod 26. The tip 60a of the opening support element 58a is rounded to a hemisphere having a radius of curvature equal to the radius of the wire from which the element is formed. Except for the area of contact, the support strut 58a cooperates with the occluder in the manner previously described, the contact area in the present embodiment being smaller at some times during the opening phase than the contact area of the previously described embodiment. Another minor difference is that in the embodiment of FIG. 7, the central depression 44 is replaced by a circular depression 44a and a raised center 45. This is, quite clearly, merely an equivalent variation of the structure previously described, although there may be some hemodynamic advantages to the preferred embodiment.

In a preferred form, the suture ring is made of a Teflon polytetrafluoroethylene pad covered with Teflon fabric, the valve ring and support rods are made of a corrosion resistant material such as Haynes 25 or stellite cobalt alloy, and the occluder, the vane 24, is made of graphite coated with a thick skin of vapor deposited pyrolytic carbon, such as occluders made and sold by Gulf Energy & Environmental Systems under the trademark PYROLITE, the manufacture and characteristics of which are well described in the prior art. Other materials may, of course, be used.

Other variations and changes in structure can be made if the essential function of the invention is preserved without departing from the scope of the invention as defined in the following claims:

I claim:

1. In a heart valve prosthesis having a valve ring, means for securing the valve ring in the place of a natural heart valve, a free floating, rotatable, discoid valve occluder and means for mounting the occluder for repetitive movement between the open and closed positions, the improvement wherein:

the valve occluder is a vane having radial symmetry about a center axis perpendicular to the general plane of the vane, and having a generally arcuate convex distal surface with a distal depression surrounding the center of the vane and having a concave proximal surface which is generally arcuate with a large arc of curvature to define a thin disc with a relatively smooth proximal surface; and the mounting means comprising opening support structure extending on the distal side of the occluder from the valve ring to the depression in the vane, the inner portion of the opening support structure extending into the depression to engage therein to control the opening movement of the occluder and to provide a knuckle-like joint between the opening support structure and the occluder during opening; and a closing support structure extending from the ring into the arcuate concavity of the proximal surface to provide a rocker-like contact support surface for the occluder during closure, the contact between the support surface and the occluder moving toward the center during closure said mounting means permitting free rotation of said occluder about its center as the occluder opens and closes.

2. The heart vane prosthesis defined in claim 1 wherein the radius of curvature of the arc of the convex distal side of the vane is approximately equal to the diameter of the vane.

3. The heart valve prosthesis defined in claim 2 wherein the radius of curvature of the arc of the concave proximal side of the vane is approximately two to three times the radius of curvature of the arc of the convex distal surface.

4. The heart valve prosthesis defined in claim 1 wherein the opening and closing support structures are so constructed and configured in respect to each other and the vane that when the vane is full open a tangent to the arcuate convex distal surface adjacent the edge thereof is approximately parallel to a central axis taken normal to the plane of the valve ring.

5. The heart valve prosthesis defined in claim 4 wherein the radius of curvature of the arc of the concave proximal side of the vane is approximately two to three times the radius of curvature of the arc of the convex distal surface.

6. The heart valve prosthesis defined in claim 5 wherein the radius of curvature of the arc of the convex distal side of the vane is approximately equal to the diameter of the vane.

7. A heart valve prosthesis, comprising:
a valve ring having a passage for blood therethrough;
means for securing the valve ring in the place of a natural heart valve;
a valve occluder in the form of a discoid vane having radial symmetry about a center axis perpendicular to the general plane of the valve occluder, and having an arcuately curved concave proximal side with a single large arc of curvature to define a thin disc with a relatively smooth proximal surface and a distal side which is generally arcuately curved and convex and has a depression therein;
distal opening support structure extending from the valve ring into the passage and then in the proximal direction into the depression in the distal side of the occluder vane to form therewith a knuckle-like joint about which the vane moves as it opens in response to pressure applied in the distal direction; and
proximal closing support structure extending from the valve ring into the passage and in the distal direction in curved configuration into the arcuate concavity of the vane to provide a rocker-like support for the vane as the vane closes in response to pressure applied in the proximal direction, the closing support being so configured in relation to the arcuate concave surface that the contact area between the closing support and the vane moves toward the center of the vane during closure thereby reducing the eccentric closing force as the valve closes;
the opening and closing support structures cooperatively defining the maximum open position of the vane such that blood flows over the arcuate convex distal surface and the arcuate concave proximal surface when the valve is opened by the pressure of blood applied in the distal direction;
the opening and closing support structures cooperating with the occluder to permit the occluder to rotate about its center axis as it opens and closes.

8. The heart valve prosthesis defined in claim 7 wherein the radius of curvature of the arc of the concave proximal side of the vane is approximately two to three times the radius of curvature of the arc of the convex distal surface.

9. The heart valve prosthesis defined in claim 8 wherein the radius of curvature of the arc of the convex distal side of the vane is approximately equal to the diameter of the vane.

10. The heart valve prosthesis defined in claim 7 wherein the opening and closing support structures are so constructed and configures in respect to each other and the vane that when the vane is full open a tangent to the arcuate convex distal surface adjacent the edge thereof is approximately parallel to a central axis taken normal to the plane of the valve ring.

11. The heart valve prosthesis defined in claim 10 wherein the radius of curvature of the arc of the concave proximal side of the vane is approximately two to three times the radius of curvature of the arc of the convex distal surface.

12. The heart valve prosthesis defined in claim 11 wherein the radius of curvature of the arc of the convex distal side of the vane is approximately equal to the diameter of the vane.

* * * * *